US011185334B2

(12) United States Patent
Lorenzo

(10) Patent No.: US 11,185,334 B2
(45) Date of Patent: Nov. 30, 2021

(54) SINGLE LUMEN REDUCED PROFILE OCCLUSION BALLOON CATHETER

(71) Applicant: DePuy Synthes Products, Inc., Raynham, MA (US)

(72) Inventor: Juan Lorenzo, Davie, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 468 days.

(21) Appl. No.: 16/368,604

(22) Filed: Mar. 28, 2019

(65) Prior Publication Data

US 2020/0305890 A1 Oct. 1, 2020

(51) Int. Cl.
| A61B 17/12 | (2006.01) |
| A61M 25/10 | (2013.01) |
| A61B 17/00 | (2006.01) |
| A61M 25/00 | (2006.01) |

(52) U.S. Cl.
CPC .. *A61B 17/12136* (2013.01); *A61B 17/12109* (2013.01); *A61B 2017/00336* (2013.01); *A61M 25/005* (2013.01); *A61M 2025/0042* (2013.01); *A61M 2025/1052* (2013.01); *A61M 2025/1079* (2013.01)

(58) Field of Classification Search
CPC ........ A61B 17/12136; A61B 17/12109; A61B 2017/00336; A61M 2025/1079; A61M 2025/1052; A61M 2025/0042; A61M 25/005; A61M 25/10185; A61M 25/1006; A61M 25/0041; A61M 2025/1063
See application file for complete search history.

(56) References Cited

U.S. PATENT DOCUMENTS

| 4,271,839 A | 6/1981 | Fogarty et al. |
| 4,441,495 A | 4/1984 | Hicswa |
| 4,446,867 A | 5/1984 | Leveen et al. |
| 5,135,486 A | 8/1992 | Eberle et al. |
| 5,141,518 A * | 8/1992 | Hess ............ A61M 25/104 604/913 |
| 5,759,173 A | 6/1998 | Preissman et al. |

(Continued)

FOREIGN PATENT DOCUMENTS

| EP | 2170452 | 4/2010 |
| EP | 3322471 | 5/2018 |
| WO | 2015065491 | 5/2015 |

*Primary Examiner* — George J Ulsh
*Assistant Examiner* — Rachel S Highland
(74) *Attorney, Agent, or Firm* — Cohen & Hildebrand, PLLC

(57) ABSTRACT

Balloon catheter devoid of guidewire or guidewire lumen and having a proximal shaft with only a single continuous lumen. A coil assembly is mounted at its proximal end to the distal end of the proximal shaft defining an interface therebetween. Disposed about a distal section of the proximal shaft and a proximal section of the coil assembly is a sleeve. A balloon, having a vent hole, forms a proximal leg seal about an outer surface of a distal end of the sleeve and an opposite distal leg seal. The sleeve covers the interface and extends axially in a distal direction terminating underneath the proximal leg seal of the balloon. A distal section of the coil assembly at least partially coincides with the distal leg seal of the balloon. A wire member secured at a plurality of connection points along the coil assembly extends axially within the balloon.

17 Claims, 3 Drawing Sheets

(56) References Cited

U.S. PATENT DOCUMENTS

| | | |
|---|---|---|
| 5,769,871 A | 6/1998 | Mers Kelly et al. |
| 5,807,331 A | 9/1998 | den Heijer et al. |
| 6,017,323 A * | 1/2000 | Chee .................. A61M 25/104 604/249 |
| 6,022,336 A | 2/2000 | Zadno-Azizi et al. |
| 6,156,005 A | 12/2000 | Theron |
| 6,423,032 B2 | 7/2002 | Parodi |
| 6,582,448 B1 | 6/2003 | Boyle et al. |
| 6,749,583 B2 | 6/2004 | Briscoe et al. |
| 6,902,540 B2 | 6/2005 | Doros et al. |
| 6,905,490 B2 | 6/2005 | Parodi |
| 6,929,634 B2 | 8/2005 | Doros et al. |
| 6,932,828 B2 | 8/2005 | Bonnette et al. |
| 6,994,718 B2 | 2/2006 | Groothuis et al. |
| 7,048,758 B2 | 5/2006 | Boyle et al. |
| 7,063,714 B2 | 6/2006 | Doros et al. |
| 7,172,621 B2 | 2/2007 | Theron |
| 7,909,794 B2 | 3/2011 | Briscoe et al. |
| 9,149,612 B2 | 10/2015 | Chuter |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,839,543 B2 | 12/2017 | Ridgley et al. |
| 10,137,231 B2 | 11/2018 | Anagnostopoulos |
| 10,137,283 B2 | 11/2018 | Kuppurathanam |
| 10,149,692 B2 | 12/2018 | Turjman et al. |
| 10,149,962 B2 | 12/2018 | Franklin et al. |
| 2002/0177870 A1* | 11/2002 | Sepetka ................. A61M 25/10 606/194 |
| 2006/0200191 A1 | 9/2006 | Zadno-Azizi |
| 2009/0111671 A1* | 4/2009 | Campbell .......... A63B 21/0603 482/148 |
| 2009/0264859 A1 | 10/2009 | Mas |
| 2012/0022426 A1 | 1/2012 | Ho et al. |
| 2014/0107575 A1 | 4/2014 | Miller et al. |
| 2014/0276585 A1 | 9/2014 | Gianotti |
| 2016/0144157 A1 | 5/2016 | Gulachenski et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Grandfield |
| 2017/0100183 A1 | 4/2017 | Iaizzo et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Fran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |

(56) References Cited

U.S. PATENT DOCUMENTS

| | | |
|---|---|---|
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367718 A1 | 12/2017 | Georgilis et al. |
| 2018/0098778 A1 | 4/2018 | Ogle |
| 2018/0169392 A1 | 6/2018 | Franklin |
| 2018/0344249 A1 | 12/2018 | McKinney et al. |
| 2018/0344993 A1 | 12/2018 | Ganz et al. |
| 2018/0369005 A1 | 12/2018 | Sanati et al. |

\* cited by examiner

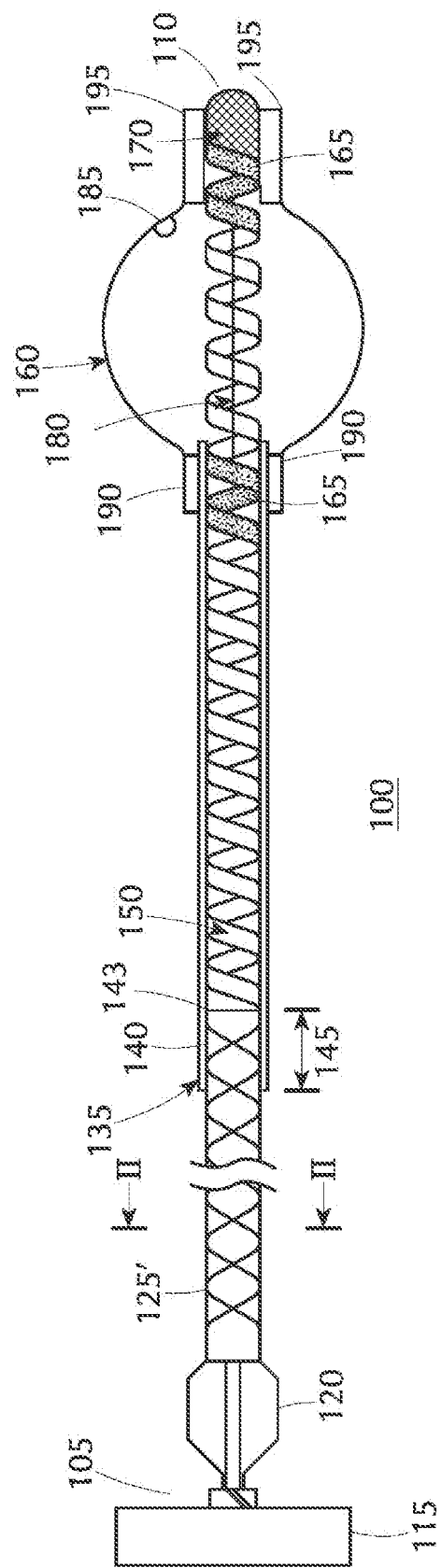
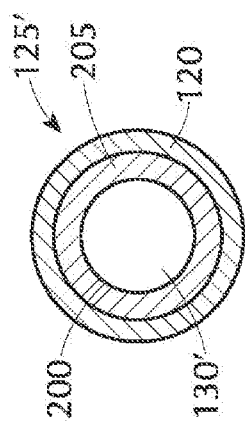
FIG. 1B
FIG. 2

SINGLE LUMEN REDUCED PROFILE OCCLUSION BALLOON CATHETER

BACKGROUND OF THE INVENTION

Field of the Invention

The present invention relates to an intravascular medical system. In particular, the present invention is directed to an improved occlusion balloon catheter eliminating the need altogether for a guidewire, a guidewire port, and a guidewire lumen.

Description of Related Art

Over-the-wire (OTW) balloon catheters and rapid exchange balloon catheters (RX) (sometimes referred to as "single operator exchange (SOE) catheters") are non-invasive devices commonly used for treatment of intravascular diseases. A typical balloon catheter comprises an elongate shaft with a balloon attached to the distal end. In use, the balloon catheter is advanced over a guidewire until the balloon is positioned at a target site adjacent a clot, blockage, occlusion, thrombosis in the diseased vessel. Once properly positioned, the balloon is inflated or expanded to dilate the opening thereby restoring blood flow through the vessel.

Specifically, OTW balloon catheters feature separate lumen, i.e., an inflation lumen and a guidewire lumen, each lumen extending the length of the catheter from respective ports at the hub (at the proximal end of the catheter) to the balloon (at the distal end of the catheter). The separate inflation and guidewire lumen may be configured longitudinally side-by-side through the catheter shaft, or coaxially as an inner tube (defining a guidewire lumen) surrounded by a coaxially disposed outer tube (defining an inflation lumen between the inner and outer tubes).

RX balloon catheters also have separate inflation lumen as well as a guidewire lumen. However, a guidewire port is positioned in an intermediate region between the hub and balloon (i.e., between the proximal and distal ends of the catheter). Thus, a guidewire lumen only extends along a portion or short section (typically about 25 cm) of the length of the catheter from the guidewire port to the balloon (at the distal end of the catheter) thereby saving time. Between the guidewire port and the balloon, the guidewire lumen is disposed separately from the inflation lumen (either side-by-side longitudinally or concentrically (similar to that discussed above for the OTW balloon)); whereas, between the hub and the guidewire port, the inflation lumen is the single lumen present in the catheter.

Each of these conventional balloon catheters having a guidewire lumen extending, partially or fully, through the catheter shaft are difficult to navigate through tortuous distal vessel pathways. It is therefore desirable to develop an improved balloon catheter that eliminates altogether the need for a guidewire port, guidewire lumen and guidewire itself.

SUMMARY OF THE INVENTION

An aspect of the present invention is directed to an improved balloon catheter that eliminates altogether the need for a guidewire port, a guidewire lumen and a guidewire itself.

Another aspect of the present invention is directed to an improved balloon catheter that eliminates altogether the need for a guidewire lumen thus maximizing the inner diameter of the catheter shaft able to accommodate a wide range of ancillary devices.

While another aspect of the present invention is directed to an improved balloon catheter that eliminates altogether the need for a guidewire lumen and as a result the balloon catheter has a reduced or lower profile (reduced outer diameter) such that it may be delivered using catheters having a smaller inner diameter lumen.

Still another aspect of the present invention relates to an improved balloon catheter having a single lumen defined axially therethrough minimizing (e.g., range of approximately 0.0165 inch to approximately 0.021 inch) the crossing profile (defined as the maximum diameter found between the proximal end of the balloon and the distal tip of the catheter) able to navigate smaller diameter distal vessels.

Yet another aspect of the present invention relates to an improved balloon catheter having a single continuous lumen defined axially therethrough able to navigate tortuous vasculature (e.g., distal vessels having a smaller diameter) without sacrificing stiffness and pushability.

Still another aspect of the present invention is directed to a balloon catheter including a proximal shaft having a proximal end, an opposite distal end with only a single continuous lumen defined axially therethrough from the proximal end to the opposite distal end; wherein the proximal shaft is devoid of a guidewire lumen. The balloon catheter also includes a coil assembly having a proximal end and an opposite distal end; the proximal end of the coil assembly mounted to the distal end of the proximal shaft defining an interface therebetween. In addition, the balloon catheter further includes a sleeve disposed about both a distal section of the proximal shaft and a proximal section of the coil assembly. Also included in the balloon catheter is a compliant balloon forming a proximal leg seal about an outer surface of a distal end of the sleeve and an opposite distal leg seal. The compliant balloon has a vent hole defined therein disposed proximally to the distal leg seal. The sleeve covers the interface and extends axially in a distal direction terminating underneath the proximal leg seal of the balloon. A distal section of the coil assembly at least partially coincides with the distal leg seal of the compliant balloon. Lastly, the balloon catheter also has a wire member extending in an axial direction within the compliant balloon, wherein the wire member is secured at a plurality of connection points along the coil assembly.

Another aspect of the present invention relates to a method for using the balloon catheter as described in the preceding paragraph. Initially, residual air is purged from the balloon catheter via the vent hole by injecting inflation media through the single continuous lumen of the proximal shaft using an inflation device connectable to a proximal end of the proximal shaft via a proximal hub. Thereafter, the compliant balloon filled with the injected inflation media is allowed to deflate. While the balloon is in a deflated state, the balloon catheter is advanced to a target site in the target vessel. Upon reaching the target site, the fluid media is dispensed through the single continuous lumen of the proximal shaft filling the compliant balloon. The balloon catheter is anchored in position by the inflated compliant balloon expanding sufficiently to physically contact an inner wall of the target vessel. As the balloon fills with the inflation media, stretching of the coil assembly in an axial direction is prevented by the wire member.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIG. 1B is an axial cross-sectional view of an alternative configuration of the present inventive balloon catheter in which the proximal shaft is a braided tube; the illustration depicting the balloon while in an expanded state;

FIG. 2 is a radial cross-sectional view of the braided tube of FIG. 1B along lines II-II.

DETAILED DESCRIPTION OF THE INVENTION

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionalist. The terms "occlusion", "thrombus", "clot" or "blockage" are used interchangeably.

The present inventive balloon catheter may be used for many vascular applications such as, but not limited to, distal vessel occlusion balloon assisted coiling; adjunctive device for distal occlusion of vessels in treatment of ischemic stroke; or opening vessels in the presence of thrombus to allow blood flow.

Figure 1A:
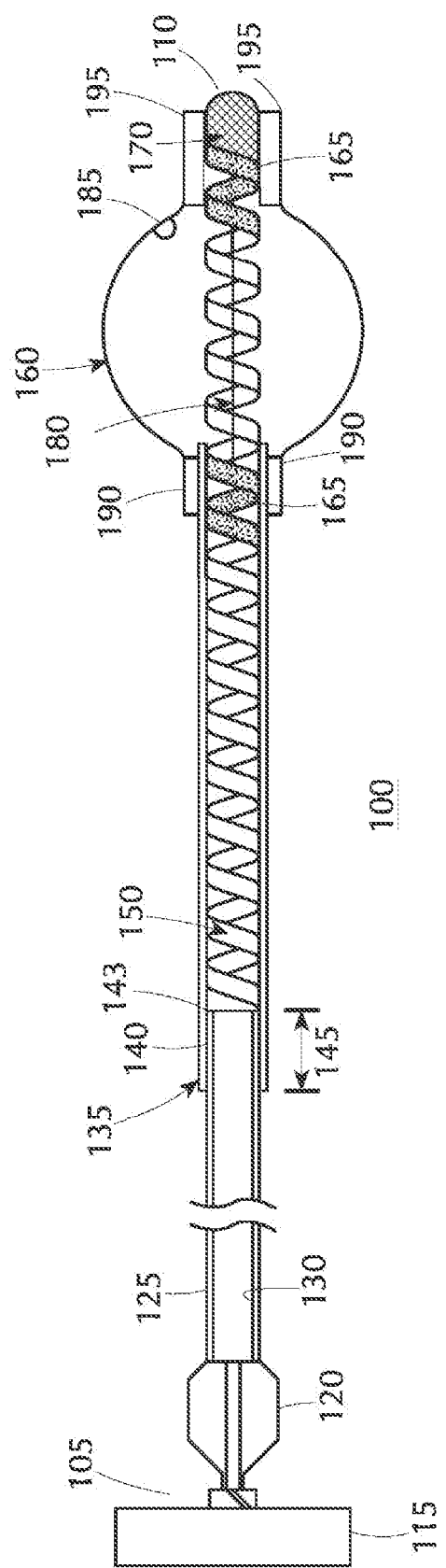
FIG. 1A is an axial cross-sectional view of one embodiment of the present inventive balloon catheter in which the proximal shaft is a tube, such as a hypotube or polyamide tube, the illustration showing the balloon in an expanded state.

Referring to FIG. 1A, the present inventive reduced or low profile (e.g., preferably in the range of approximately 0.0165 inch to approximately 0.021 inch), closed terminus catheter 100 has a single continuous lumen 130 extending axially a full length of the catheter from a proximal end 105 to an opposite distal end 110. Prior to introduction into the body, the distal end of the balloon catheter may be pre-bent or deformed into a desired curve shape (e.g., J-shape) depending on the tortuous vessel to be navigated. The need for a guidewire in the present inventive configuration has been eliminated altogether. Because the present inventive balloon catheter is not delivered to a target site by tracking over a guidewire, the configuration is devoid, free from, does not include, and hence excludes a guidewire lumen extending, either partially or fully, through any section of the catheter as well as eliminating the need for a guidewire itself and guidewire port. At the proximal end 105 of the catheter 100 is a proximal shaft 125 or a pusher device in which the single continuous lumen 130 is defined axially therethrough. In an exemplary embodiment illustrated in FIG. 1A, the proximal shaft 125 is a tube shaft through which a single continuous lumen 130 is defined axially its proximal end to its opposite distal end. Lumen 130 serves exclusively as an inflation lumen for dispensing therethrough an inflation media (e.g., 50% contrast saline solution). The tube shaft may be a hypotube defined as hypodermic tubing made of biocompatible metal such as Nitinol or stainless steel. Proximal shaft 125 may alternatively be tubing made of a biocompatible polymer such as polyamide (Nylon) tubing.

Connected to the proximal end 105 of the proximal shaft 125 is a proximal hub or connector 120 to which an ancillary device 115 such as an inflation device (e.g., syringe) can be attached for dispensing under pressure the inflation media (e.g., 50% contrast saline solution) through the single lumen 130.

A sleeve or extrusion 135 made of (e.g., made of a polymeric material such as Nylon, Nylon blend or other biocompatible polymer) has a proximal end and an opposite distal end with a single lumen 140 defined axially therethrough. It is also contemplated and within the intended scope of the present invention for the sleeve or extrusion 135 to be made of a biocompatible metal (e.g., Nitinol or stainless steel) visible during imaging due to its radiopacity. An inner diameter of the single lumen 140 of the sleeve 135 is sized to accommodate an outer diameter of the distal end of the proximal shaft 125 telescopically slidable in an axial direction therein creating an axial overlap or interface 145 between the two components. Disposed within the single lumen 140 of the sleeve 135 in an axial direction distally beyond the distal end of the proximal shaft 125 is a coil assembly. A proximal end of the coil assembly is circumferentially bonded, adhered, welded or otherwise attached to the distal end of the proximal shaft 125 at a junction or interface 143. The coil assembly includes a non-radiopaque coil 150. Preferably, a flat wire spiral coil 150 made of Nickle-Titanium (Nitinol), stainless steel or other biocompatible metal whose pitch coil width preferably varies in a range from approximately 0.002 inch to approximately 0.010 inch in an axial direction to vary the stiffness of the coil. One or more, preferably two, radiopaque marker segments 165 are employed to delineate the axial length of the balloon when subject to X-ray imaging. Radiopaque marker segments 165, preferably coiled flat wire segment made of a radiopaque material (e.g., a platinum alloy), are circumferentially welded proximate the distal portion at locations (separated a predetermined distance from one another) along the non-radiopaque coil 150 to provide markers visible under X-ray imaging for the purpose of indicating in vivo positioning of a balloon or inflating member 160. Together the non-radiopaque spiral coil 150 and radiopaque marker segments 165 represent the coil assembly. In FIG. 1A, two radiopaque marker segments 165 are disposed along the non-radiopaque spiral coil 150 in regions coinciding with respective proximal and distal sides/legs of the balloon 160 in an axial direction. Starting proximally to the junction or interface 143 and extending in a distal direction, the sleeve 135 is molded about a distal portion of the proximal shaft 125 and a proximal portion of the non-radiopaque spiral coil 150. A distal end of the sleeve 135 terminates beneath a proximal leg or seal of the balloon 160.

Sheathed over a section of the coil assembly including a portion of the non-radiopaque spiral coil 150 and the radiopaque marker segments 165 mounted thereto is the balloon 160 made of a flexible, compliant axially oriented biocompatible material, e.g. silicone or urethane. In an axial direction, the balloon 160 is sealed in a proximal region (i.e., proximal seal/leg 190) about an outer surface of the distal end of the sleeve or extrusion 135, and in an opposite distal region the balloon is sealed (i.e., distal seal/leg 195) forming a closed terminus in order to maintain pressure within the balloon. A vent hole 185 is defined in the balloon 160 proximally of the distal seal/leg 195. Prior to implantation in the body, the balloon catheter is prepped to expunge residual air, as described in further detail below.

Respective proximal and distal sides/leg seals 190, 195 of the balloon 160 may be formed by an adhesive chemical bond, a heat bond and/or a mechanical crimping of a distal section sleeve over the balloon. The distal end of the sleeve or extrusion 135 terminates beneath the proximal side/leg seal 190 on the proximal side of the balloon. A distal seal 170, for example, an adhesive, fuse seal or cap (e.g., polymer cap), seals a distal side of the balloon 160 to the distal end of the coil assembly as well as blocking/sealing the lumen of the coil assembly forming a closed terminus thereby maintaining pressure within the volume of the sealed balloon. In an alternative configuration where the seal is a mechanical crimp, the distal side/leg seal 195 of the balloon is mechanically crimped to a distal sleeve section (e.g., washer, band or ring) made of the same or different material from that of the proximal section of sleeve or extrusion 135.

A wire member 180 is disposed axially within the balloon. Specifically, wire member 180 is secured at respective points to the coil assembly coinciding with respective proximal and distal sides/legs of the balloon 160. Wire member 180 serves a dual function: one function carried out during positioning of the balloon catheter at the target site prior to inflation of the balloon, the other function served during inflation of the balloon itself once properly positioned at the target site. Prior to being introduced into the body wire member 180 may be shaped or bended to a desired configuration (e.g., J-shape), thereby aiding in tracking or advancement of the deflated balloon through a tortuous pathway to a desired target site in the vessel while simultaneously imparting rigidity to the deflated balloon. Once the catheter has been positioned at a desired target site in the vessel the balloon is inflated with the inflation media. During inflation the balloon expands both radially and axially. Such axial stretching of the coil assembly could otherwise sacrifice the integrity of the distal side/leg seal of the balloon. The wire member 180 of the present inventive balloon catheter configuration serves the dual or second function of preventing or prohibit axial stretching of the coil assembly during inflation of the balloon. In FIG. 1A, wire member 180 is secured at each end to respective radiopaque marker band segments 165. Alternatively, the wire member 180 may be attached between two regions axially along the coil assembly in respective proximal and distal areas coinciding with the proximal side/leg seal 190 of the balloon at the distal end of the sleeve or extrusion 135 and the distal side/leg seal 195 of the balloon proximate the distal end of the coil assembly.

An alternative construction is depicted in FIG. 1B wherein the proximal shaft or pusher is a braided tube 125' having a single lumen 130' extending axially therethrough. FIG. 2 is a radial cross-sectional view of the braided tube 125' of FIG. 1B along lines II-II depicted as comprising a fused assembly of an inner liner (in the shape of a braid) 200 and an outer jacket 205 made of a biocompatible polymer such as polyimide.

Figure 1C:
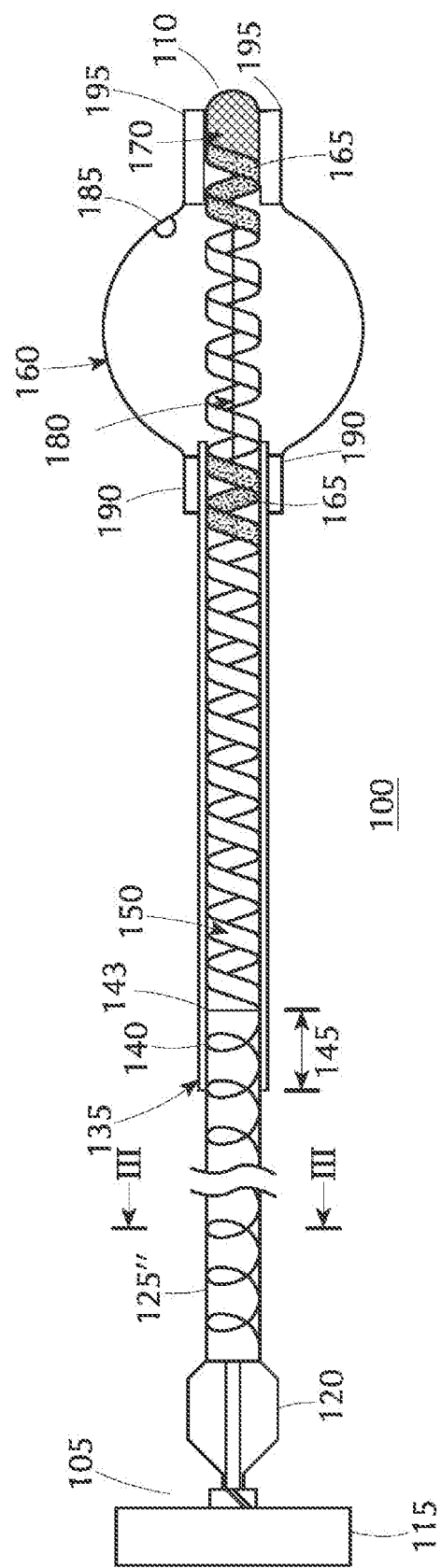
FIG. 1C is an axial cross-sectional view of yet another embodiment of the present inventive balloon catheter in which the proximal shaft is a coiled tube; the illustration depicting the balloon while in an expended state.
Figure 3:
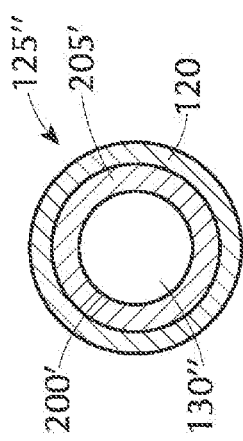
FIG. 3 is a radial cross-sectional view of the coiled tube of FIG. 1C along lines III-III.

FIG. 1C depicts the design of the proximal shaft as a coiled tube 125" having a single lumen 130" extending axially therethrough. FIG. 3 is a radial cross-sectional view of the coiled tube 125" of FIG. 1C along lines III-III depicted as comprising a fused assembly of an inner liner (in the shape of a spiral coil) 200' and an outer jacket 205' made of a biocompatible polymer such as polyimide.

In operation, prior to being introduced into the body, the present inventive balloon catheter is prepped by purging or exhausting residual air residing in the balloon catheter through the vent hole 185 defined in the balloon 160 proximally of the distal side/leg seal 195. The diameter of the vent hole 185, preferably less than or equal to approximately 0.001 inch, is sized sufficiently large to allow residual air to pass from the balloon, yet small enough to prohibit escape of liquid (e.g., inflation media) therethrough. Air having a lower viscosity than the inflation media is such that the vent hole size allows only the residual air to escape therethrough. Syringe 115 connected to the proximal hub 120 dispenses under pressure the inflation media (e.g., 50% contrast saline solution) through the inflation lumen 130 and into the balloon 160. As the inflation media fills the catheter any residual air residing in the lumens 130, 140 and balloon 160 is pushed distally and exits from the catheter via the vent hole 185. Rather than remain open, a material or membrane may be positioned in the vent hole to allow the passage therethrough of only the residual air, inhibiting passage of any liquid (e.g., inflation media). Once the balloon has been inflated with the inflation media thereby expelling any residual air via the vent hole 185, contracting characteristics of the balloon together with ambient pressure cause the balloon to deflate on its own.

Now that the catheter has been properly prepped, it may be safely introduced into the body. Prior to introduction of the catheter into the body, pre-shaping or pre-bending (e.g., into a J-shape) of the wire member 180 disposed within the deflated balloon 160 may assist in tracking the tortuous distal vessel pathway to a target site. While the balloon 160 is in a compressed/deflated state (having a reduced or minimized outer diameter) the present inventive balloon catheter is advanced through the vessel to a target site of the clot, blockage, occlusion or thrombus. Upon reaching the target site, balloon 160 is expanded/inflated (having an enlarged or maximized outer diameter) by attaching to the proximal hub 120 the inflation device 115 (e.g., syringe) containing the inflation media (e.g., typically a 50% contrast saline solution) dispensed under pressure through the single lumen 130 (inflation lumen) defined in the proximal shaft 125. As the inflation media continues to be introduced, the outer diameter of the balloon 160 expands/inflates in size until physically contacting the inner wall of the vessel (thereby anchoring its location) temporarily occluding blood flow distally beyond the balloon 160. Wire member 180 disposed within the balloon prevents or prohibits the compliant elastomeric material (e.g., silicone or polyurethane) from expanding in an axial direction as the balloon fills with the inflation media. The reduced profile and flexibility of the present inventive device in combination with its ability to be advanced through the tortuous pathway of the vessel makes the catheter particularly suitable to be positioned and inflated on a side branch blocking advancement therein of emboli produced during procedures performed on the main vessel.

The reduced profile of the device as a result of the catheter having only a single lumen (serving exclusively as an inflation lumen) (eliminating the need for a guidewire lumen and guidewire) provides a flexible construction allowing access of tortuous distal vessels without sacrificing stiffness and pushability. The present inventive balloon catheter due to its reduced profile, pushability and torquability can be either delivered/advanced by itself or tracked though a microcatheter to a desired target site in a vessel. The sleeve acts as a liner providing stiffness and stability. In addition, because the balloon is sealed about the outer surface of the sleeve the balloon is able to be pressurized (distended or enlarged), without expansion of the sleeve.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A balloon catheter comprising:
    a proximal shaft having a proximal end, an opposite distal end with only a single continuous lumen defined axially therethrough from the proximal end to the opposite distal end; wherein the proximal shaft is devoid of a guidewire lumen;
    a coil assembly having a proximal end and an opposite distal end; the proximal end of the coil assembly mounted to the distal end of the proximal shaft defining an interface therebetween;
    a sleeve disposed about both a distal section of the proximal shaft and a proximal section of the coil assembly; and
    a compliant balloon forming a proximal leg seal about an outer surface of a distal end of the sleeve and an opposite distal leg seal; the compliant balloon having a vent hole defined therein disposed proximally to the distal leg seal; the sleeve covering the interface and extending axially in a distal direction terminating underneath the proximal leg seal of the compliant balloon; a distal section of the coil assembly at least partially coinciding with the distal leg seal of the compliant balloon; and
    a wire member extending in an axial direction within the compliant balloon; the wire member is secured at a plurality of connection points along the coil assembly.

2. The balloon catheter according to claim 1, wherein the proximal shaft is a hypotube, a tube, a braided tube, or a coiled tube.

3. The balloon catheter according to claim 2, further comprising:
    an inflation device connectable to the proximal end of the proximal shaft via a proximal hub; the inflation device being in fluid communication with the single continuous lumen of the proximal shaft for exclusively dispensing an inflation media.

4. The balloon catheter according to claim 1, wherein the coil assembly comprises a coil made of non-radiopaque material and marker segments made of radiopaque material secured to the coil made of non-radiopaque material; each of the radiopaque marker segments coinciding with the proximal and distal leg seals, respectively, of the compliant balloon.

5. The balloon catheter according to claim 1, further comprising a distal cap to which the distal end of the coil assembly is mounted; the distal leg seal of the compliant balloon is mounted to the distal cap.

6. The balloon catheter according to claim 1, wherein the plural connection points of the wire member are first and second connection points disposed proximate the proximal and distal leg seals, respectively, of the compliant balloon.

7. The balloon catheter according to claim 1, wherein a distal tip of the wire member is deformed into a J-shape.

8. The balloon catheter according to claim 1, wherein the vent hole has a diameter less than or equal to approximately 0.001 inch.

9. The balloon catheter according to claim 1, wherein a stiffness of the coil assembly varies in an axial direction.

10. A method for using a balloon catheter to occlude blood flow in a target vessel; wherein the balloon catheter includes: a proximal shaft having a proximal end, an opposite distal end with only a single continuous lumen defined axially therethrough from the proximal end to the opposite distal end; wherein the proximal shaft is devoid of a guidewire lumen; a coil assembly having a proximal end and an opposite distal end; the proximal end of the coil assembly mounted to the distal end of the proximal shaft defining an interface therebetween; a sleeve disposed about both a distal section of the proximal shaft and a proximal section of the coil assembly; and a complaint balloon forming a proximal leg seal about a distal end of the sleeve and an opposite distal leg seal; the compliant balloon having a vent hole defined therein disposed proximally to the distal leg seal; the sleeve covering the interface and extending axially in a distal direction terminating underneath the proximal leg seal of the compliant balloon; a distal section of the coil assembly at least partially coinciding with the distal leg seal of the compliant balloon; and a wire member extending in an axial direction within the compliant balloon; the wire member is secured at a plurality of connection points along the coil assembly; the method comprising the steps of:
    purging residual air from the balloon catheter via the vent hole by injecting inflation media through the single continuous lumen of the proximal shaft using an inflation device connectable to the proximal end of the proximal shaft via a proximal hub;
    allowing the compliant balloon filled with the injected inflation media to deflate;
    while the compliant balloon is in a deflated state, advancing the balloon catheter to a target site in the target vessel;
    upon reaching the target site, dispensing the fluid media through the single continuous lumen of the proximal shaft and filling the compliant balloon;
    anchoring of the balloon catheter in position by the inflated compliant balloon expanding sufficiently to physically contact an inner wall of the target vessel; and
    as the compliant balloon fills with the inflation media, stretching of the coil assembly in an axial direction is prevented by the wire member.

11. The method in accordance with claim 10, wherein the proximal shaft is a hypotube, a tube, a braided tube, or a coiled tube.

12. The method in accordance with claim 10, wherein the coil assembly comprises a coil made of non-radiopaque material and marker segments made of radiopaque material secured to the coil made of non-radiopaque material; each of the radiopaque marker segments coinciding with the proximal and distal leg seals, respectively, of the compliant balloon.

13. The method according to claim 10, wherein the balloon catheter further comprises a distal cap to which the distal end of the coil assembly is mounted; the distal leg seal of the compliant balloon is mounted to the distal cap.

14. The method according to claim 10, wherein the plural connection points of the wire member are first and second connection points disposed proximate the proximal and distal leg seals, respectively, of the compliant balloon.

15. The method according to claim 10, wherein prior to the advancing step, further comprising the step of deforming the wire member into a J-shape.

16. The method according to claim 10, wherein the vent hole has a diameter less than or equal to approximately 0.001 inch.

17. The method according to claim 10, wherein a stiffness of the coil assembly varies in an axial direction.

* * * * *